(12) United States Patent
Tarca et al.

(10) Patent No.: US 11,701,243 B2
(45) Date of Patent: Jul. 18, 2023

(54) APPARATUSES AND METHODS FOR MILLING BONE

(71) Applicant: Tarca LLC, Belle Mead, NJ (US)

(72) Inventors: Thomas William Tarca, Belle Mead, NJ (US); Sandra Lee Tarca, Belle Mead, NJ (US); Reuben Quincey Zielinski, Fishers, IN (US); Robert Anderson Till, Avon, IN (US)

(73) Assignee: Tarca LLC, Belle Mead, NJ (US)

( * ) Notice: Subject to any disclaimer, the term of this patent is extended or adjusted under 35 U.S.C. 154(b) by 750 days.

(21) Appl. No.: 16/573,502

(22) Filed: Sep. 17, 2019

(65) Prior Publication Data

US 2020/0085591 A1 Mar. 19, 2020

Related U.S. Application Data

(60) Provisional application No. 62/732,076, filed on Sep. 17, 2018.

(51) Int. Cl.
*A61F 2/46* (2006.01)
*B02C 18/24* (2006.01)
*B02C 18/14* (2006.01)

(52) U.S. Cl.
CPC .......... *A61F 2/4644* (2013.01); *B02C 18/145* (2013.01); *B02C 18/24* (2013.01); *A61F 2002/4645* (2013.01)

(58) Field of Classification Search
CPC ........... A61F 2002/4645; A61F 2/4644; A61B 2017/1602; A47J 43/255
See application file for complete search history.

(56) References Cited

U.S. PATENT DOCUMENTS

| | | | | | |
|---|---|---|---|---|---|
| 125,428 | A | * | 4/1872 | Amerling | A47J 43/255 241/273.2 |
| 2,570,945 | A | * | 10/1951 | Hawkins | B23B 49/005 408/226 |
| 4,710,075 | A | * | 12/1987 | Davison | A61B 17/16 408/202 |
| 5,096,344 | A | * | 3/1992 | Fischer | E21B 10/445 175/323 |

(Continued)

FOREIGN PATENT DOCUMENTS

| FR | 2712483 A1 | * | 5/1995 | ........... A61F 2/4644 |
|---|---|---|---|---|
| WO | WO-03017913 A1 | * | 3/2003 | ........... A61F 2/4601 |
| WO | WO-2006105950 A2 | * | 10/2006 | ........... A61F 2/4644 |

*Primary Examiner* — David W Bates
(74) *Attorney, Agent, or Firm* — Maginot, Moore & Beck LLP

(57) ABSTRACT

A bone mill includes a housing, at least a first bone milling tool, a proximal bearing sleeve, and a distal bearing sleeve. The housing defines a work chamber. The work chamber has a first axial end, a second axial end, a feed input opening, and an output opening. The bone milling tool is configured to be disposed within the work chamber, and extends at least from a first axial end to the second axial chamber. The proximal bearing sleeve is supported by the housing proximate the first axial end, and a distal bearing sleeve supported by the housing proximate the second axial end. The proximal bearing sleeve and the distal bearing sleeve support the bone milling tool and allow rotation of the bone milling tool within the work chamber about an axis.

12 Claims, 16 Drawing Sheets

(56) References Cited

U.S. PATENT DOCUMENTS

| | | | | |
|---|---|---|---|---|
| 5,918,821 | A * | 7/1999 | Grooms | B02C 19/0056 |
| | | | | 241/285.2 |
| 5,954,463 | A * | 9/1999 | Jore | B25B 23/00 |
| | | | | 81/439 |
| 6,287,312 | B1 * | 9/2001 | Clokie | B02C 19/0056 |
| | | | | 606/85 |
| D537,938 | S * | 3/2007 | Hay | D24/133 |
| 7,635,101 | B1 * | 12/2009 | Mah | A47J 43/255 |
| | | | | 241/92 |
| 8,857,749 | B2 * | 10/2014 | Hay | A61F 2/4644 |
| | | | | 241/260.1 |
| 9,636,235 | B2 * | 5/2017 | Hensler | B65D 51/26 |
| 2004/0210229 | A1 * | 10/2004 | Meller | A61B 17/1635 |
| | | | | 606/80 |
| 2004/0232631 | A1 * | 11/2004 | Chen | B25B 21/007 |
| | | | | 279/75 |
| 2005/0135889 | A1 * | 6/2005 | Turrini | B23B 51/0081 |
| | | | | 408/230 |
| 2006/0138260 | A1 * | 6/2006 | Hay | B02C 19/0056 |
| | | | | 241/93 |
| 2008/0161649 | A1 * | 7/2008 | Deshmukh | B02C 19/0056 |
| | | | | 241/199.12 |
| 2009/0157082 | A1 * | 6/2009 | Meredith | A61F 2/46 |
| | | | | 606/84 |
| 2010/0004653 | A1 * | 1/2010 | Rasekhi | B02C 19/0056 |
| | | | | 606/85 |
| 2015/0101177 | A1 * | 4/2015 | Hall | B25B 21/007 |
| | | | | 408/113 |

* cited by examiner

APPARATUSES AND METHODS FOR MILLING BONE

This application claims the benefit of U.S. provisional patent application Ser. No. 62/732,076, filed Sep. 17, 2018, the entirety of which is incorporated herein by reference.

TECHNICAL FIELD

This invention relates generally to apparatuses and methods for milling of bone extracted from a body.

BACKGROUND OF THE INVENTION

Currently, there are over 60 million surgeries performed in the U.S. alone, many of which are on the spine, maxillofacial, orthopedic, or some other musculoskeletal area. For example, in one recent year, the number of such orthopedic surgeries was roughly 5.3 million, and that number is expected to grow to 6.6 million shortly. Over 25,000 orthopedic surgeons currently practice in the United States.

Orthopedic surgical procedures often require a bone mill to mill bone particles that are either allografts (cadavers) or autografts (patients' body). These milled particles are used for bone pastes, mixed together with bone cement, and used altogether as either bone repair or bone filler material during the surgical procedures. For many of these procedures the amount of milled bone required is often too little to justify an industrial style bone mill. Moreover, there is always a risk of disease associated with re-using bone milling equipment. Furthermore, these current industrialized bone mills require significant capital for the base unit in addition to purchasing sterile disposable blades.

One alternative to industrial, reusable bone mills is a disposable bone mill. Disposable bone mills are manually rotated, inexpensive, are one-time use, and require no cleaning or sterilization. In the United States there has been a directed increase in the number of orthopedic procedures shifting from inpatient hospital settings to smaller outpatient Ambulatory Surgery Centers (ASC's). Over the next decade, inpatient procedures are expected to decrease two percent while outpatient volumes will likely grow fifteen percent across the U.S. As the government and payers scrutinize costs and push the shift to value-based care, outpatient surgery is expected to see an overall eleven percent increase from 2017 to 2022. The benefits of utilizing a completely disposable bone mill for an outpatient facility eliminates the excessive costs of capital and adequate equipment and resources to sterilize the large industrial units.

Medical device manufacturers have capitalized on the use of rigid plastic parts for these types of products which allow a low-cost product option that can be safely sterilized and then disposed of.

Sterilizable, reusable bone mills are in wide use in hospital based settings. However, the sterilization process can be compromised by human error. As a consequence, a reused bone mill may not be 100% clean, bio-burden, and germ free. Moreover, such reusable bone mills have self-contained power, and thus lack control of manually rotated mills from the human touch and feel. Another drawback of powered mills is that users and operating room personnel have a tendency to set the reusable bone mill at higher revolutions in an attempt to speed the bone milling process up, however, these actions may cause excessive heating of the bone which can lead to cell structure damage of the milled bone.

Although manual disposable mills address the drawbacks of reusable powered mills, the existing disposable bone mills also have their own shortcomings. Physician assistants can spend significant time in surgeries manually rotating disposable bone mills to create the milled bone for repair on a patient. Due to the sensitive time nature and risk of infection during the surgeries, it is desirable to complete the procedures as fast as possible. This can then require many turns of the manually operated bone mill resulting in complaints due to fatigue as a result of the twisting motion and added downward force on the bone feedstock.

In the conventional art of disposable bone mills, a metalized mill is mounted (over-molded) into a manually operated rotary handle and this subassembly is captivated by a bone mill body. The bone mill body consists of a feedstock shoot and milled bone collection pocket. Due to the forces exerted on the bone mill as a result of the intended use, the bone mill tends to jam as a result of the over-molded plastic deforming. Moreover, the metalized mill is sub-optimal for the milling of bone and causes the user to exert more force than required to mill the bone.

There is a need, therefore, for a new bone milling technique and associated apparatus that addresses one or more shortcomings of the prior art.

SUMMARY OF THE INVENTION

At least one of the embodiments described herein include a bone mill having features that provide a better, sturdier, more consistent milling of the bone as well as a simple way to power the bone mill with a powered tool used in the operating room.

A first embodiment is a bone milling tool having at least a first bone milling tool bit and a tool bit housing. The tool bit housing includes an actuator and a tool mount. The bone milling tool bit is directly and securely fastened to the tool mount, and the actuator is rigidly secured to the tool mount. The actuator includes a power tool interface configured to receive a rotating drive mechanism of a powered tool and impart the rotation of the rotating drive mechanism to the first bone milling tool bit through the tool mount.

A second embodiment is a bone mill that includes a housing, a bone milling tool, a proximal bearing sleeve, and a distal bearing sleeve. The housing defines a work chamber. The work chamber has a first axial end, a second axial end, a feed input opening, and an output opening. The bone milling tool is configured to be disposed within the work chamber, and extends at least from a first axial end to the second axial chamber. The proximal bearing sleeve is supported by the housing proximate the first axial end, and a distal bearing sleeve supported by the housing proximate the second axial end. The proximal bearing sleeve and the distal bearing sleeve support the bone milling tool and allow rotation of the bone milling tool within the work chamber about an axis.

In some embodiments, a feature is added to the handle to allow manual or powered milling of the bone. In other embodiments, a work chamber design is employed to further reduce the propensity of bone fragment jamming, while in still other embodiments, a scavenging channel and scraping appendage is used to harvest the milled bone off the milling tool bit.

BRIEF DESCRIPTION OF THE DRAWINGS

Some of the figures shown herein may include dimensions or may have been created from scaled drawings. However, such dimensions, or the relative scaling within a figure, are by way of example only, and not to be construed as limiting the scope of this invention.

DESCRIPTION OF THE ILLUSTRATED EMBODIMENTS

Figure 1:
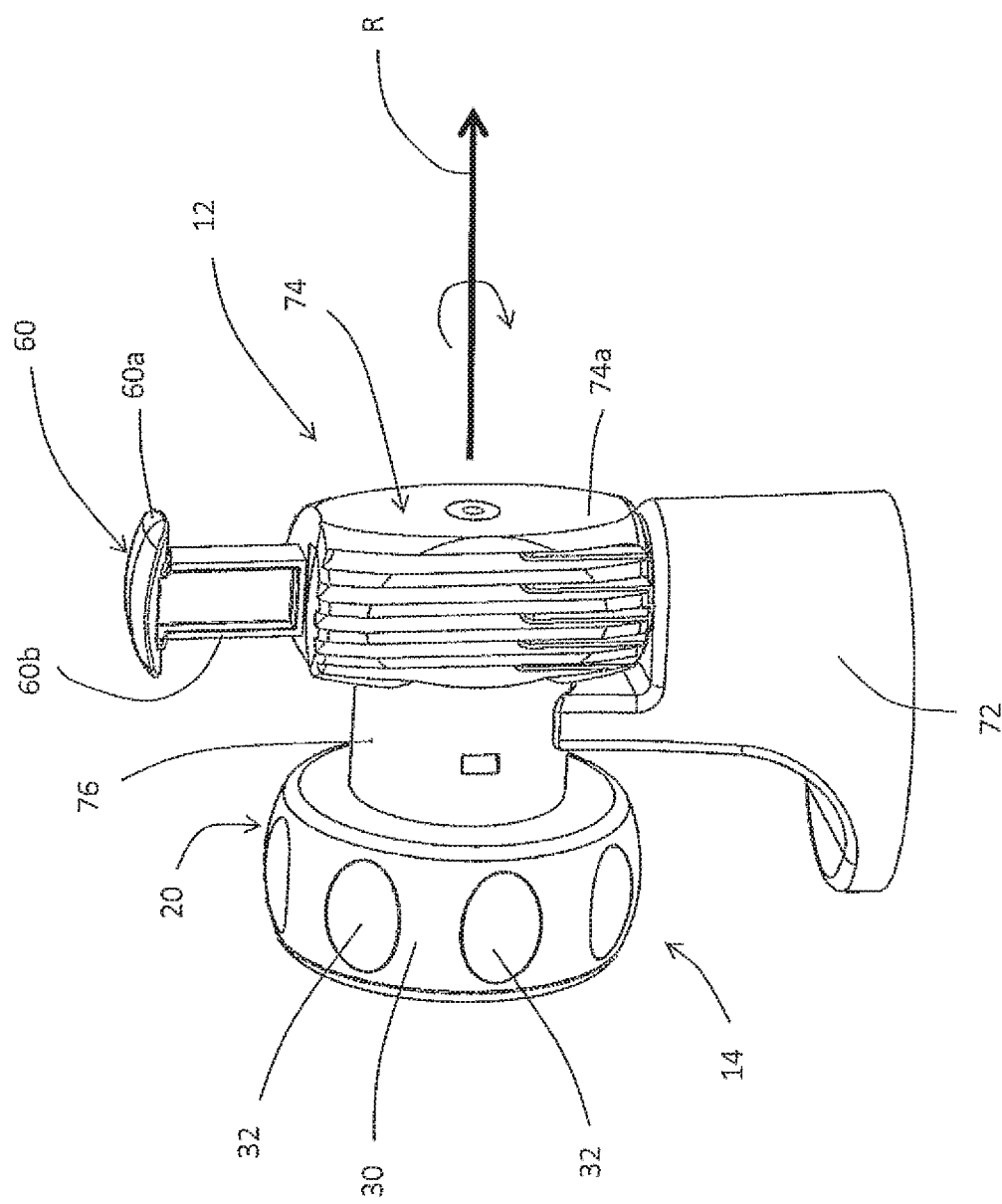
FIG. 1 shows a front and side perspective view of an exemplary embodiment of a bone mill according to the invention.

For the purposes of promoting an understanding of the principles of the invention, reference is made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Figure 2:
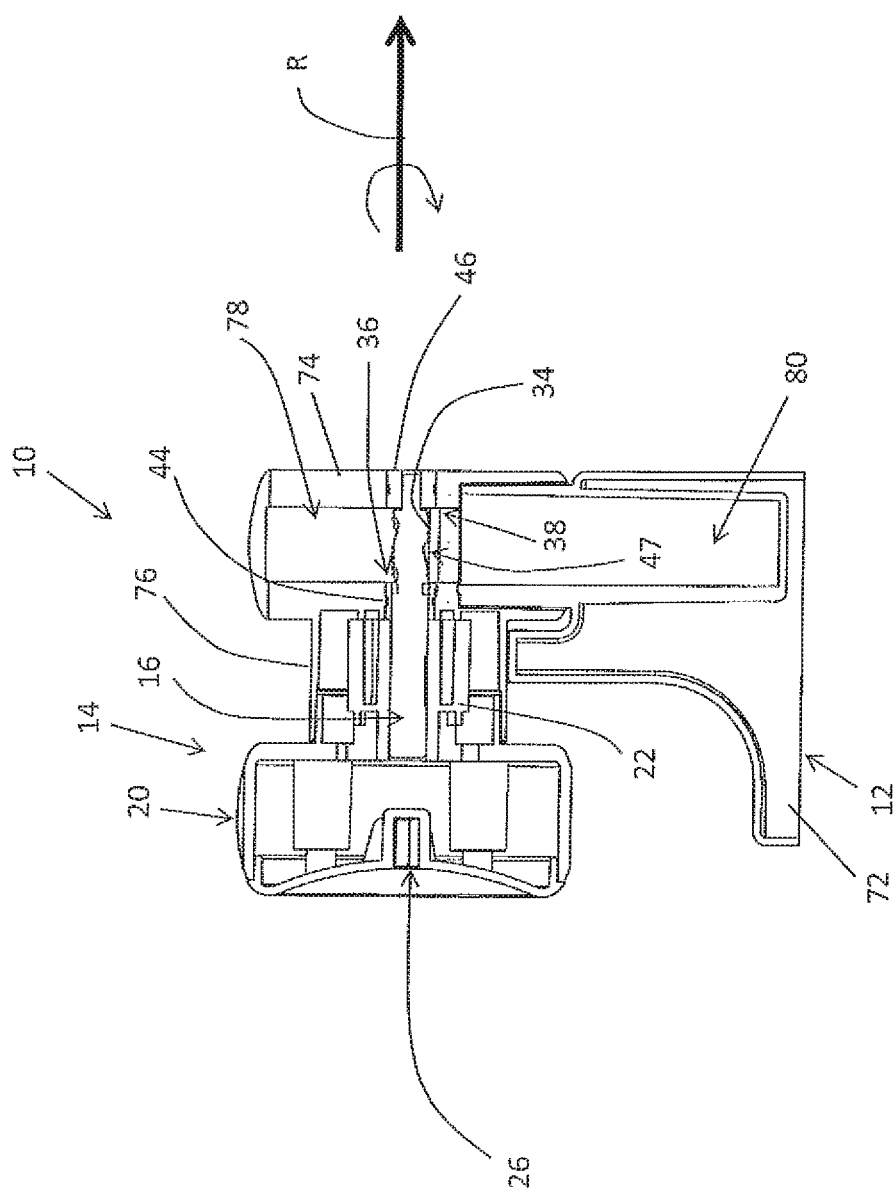
FIG. 2 shows a side cutaway view of the bone mill of FIG. 1.

FIG. 1 shows a perspective view of a first exemplary embodiment of a bone mill 10. FIG. 2 shows a side cutaway view of the bone mill 10. With reference to both FIG. 1 and FIG. 2, the bone mill 10 includes a housing 12 and a bone milling tool 14. The housing 12 includes a work chamber 34, a base 72, a barrel 74 a cylinder 76, a feed chamber 78 and a collection chamber 80. The base 72 is generally configured to support the barrel 74 and the cylinder 76, and contains at least a part of the collection chamber 80. The barrel 74 extends along the axis of rotation R and forms a housing around the work chamber 34, the feed chamber 78, and a part of the collection chamber 80. The cylinder 76 extends axially from the rear of the barrel 74, and forms a receptacle for receiving the bone milling tool 14. The barrel 74 includes a front side 74a, opposite the side from the cylinder 76 extends.

Figure 3:
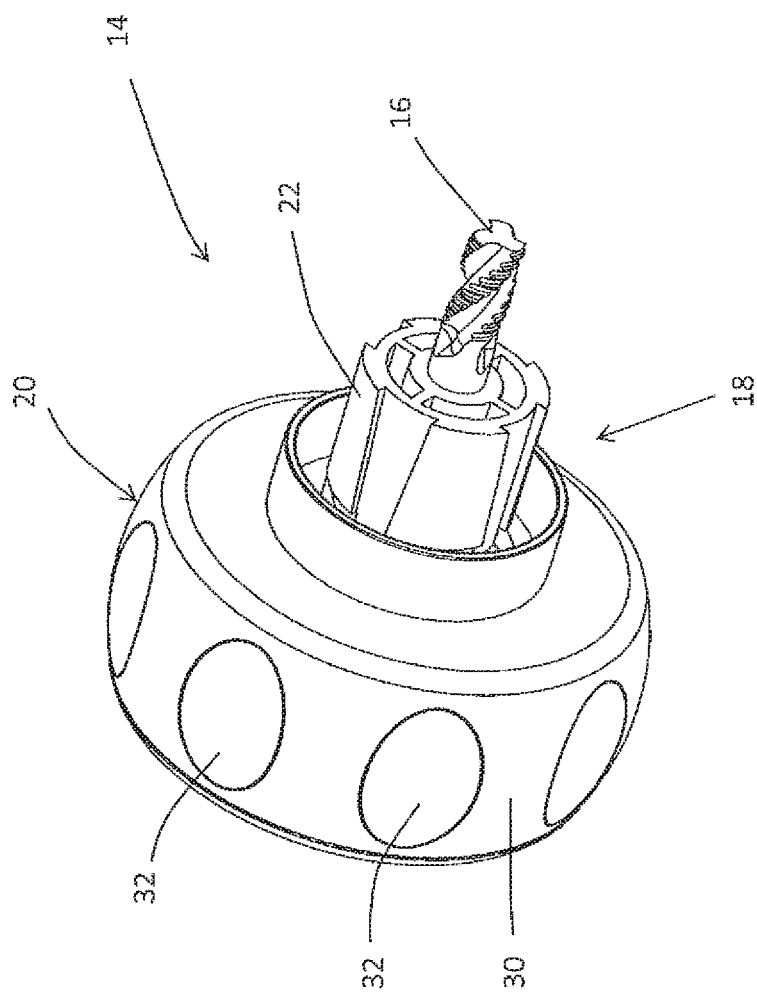
FIG. 3 shows a front perspective view of the bone milling tool of the bone mill of FIG. 1.
Figure 4:
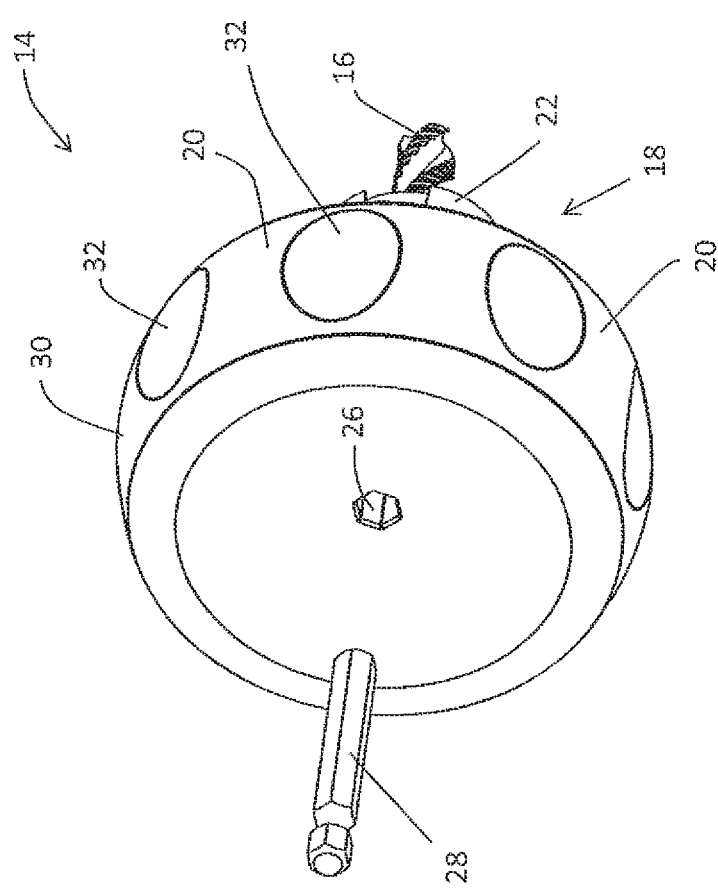
FIG. 4 shows a rear perspective view of the bone milling tool of FIG. 13.

FIGS. 3 and 4 show the bone milling tool 14 in further detail. FIG. 3 shows a front perspective view of the bone milling tool 14, and FIG. 4 shows a rear perspective view of the bone milling tool 14. With reference to FIGS. 1-4, the bone milling tool includes a bone milling tool bit 16 and a tool bit housing 18. The tool bit housing 18 includes an actuator 20 and a tool mount 22.

Figure 5:
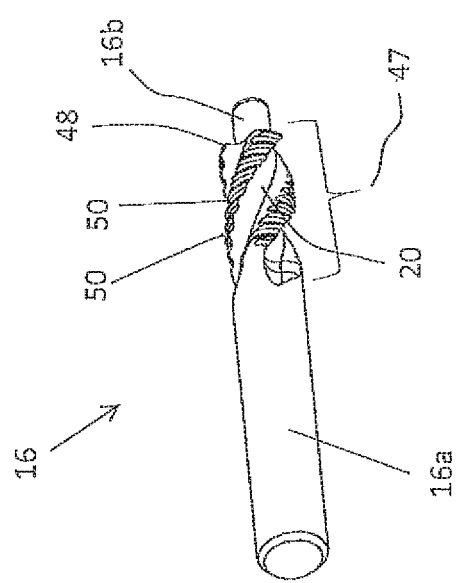
FIG. 5 shows a perspective view of an exemplary bone milling tool bit that may be used in the bone milling tool of FIG. 3.

FIG. 5 shows a perspective view of the tool bit 16 without the tool bit housing 18. Referring to FIG. 5, the tool bit 16 is a metalized bit having an axial shaft or shank 16a, a set of fluted lands 48, and a distal bearing journal 16b. Each of the lands 48 in this embodiment extends in a spiral manner between the shank 16a and the distal bearing journal 16b, and has a plurality of grinding teeth 50. Collectively, the lands 48 and grinding teeth 50 form an axially extending grinding portion 47 between the shank 16a and the bearing journal 16b. It will be appreciated that the splines or lands 48 and teeth 50 may take other forms to allow for different size bone fragments.

Figure 6:
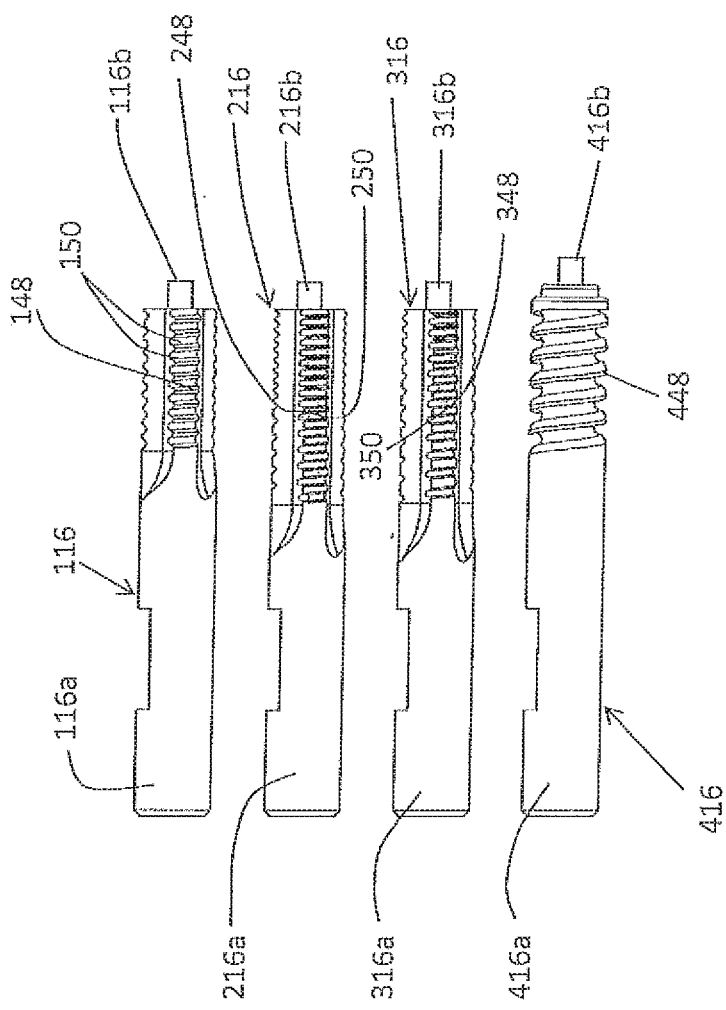
FIG. 6 shows four alternative bone milling tool bits that may be used in the bone milling tool of FIG. 3.

For example, FIG. 6 shows four variant milling tool bits 116, 216, 316 and 416 that may be used for different purposes. Each of the tool bits 116, 216, and 316 is a metalized bit having a respective shank 116a, 216a, and 316a, a respective set of fluted lands 148, 248, and 348, and a respective distal bearing journal 116b, 216b, and 316b. The tool bit 416 has a shank 416a, a spiral land 448, and a distal bearing journal 416b. Thus, the grinding portion of the tool bit 416 does not include multiple teeth on multiple lands. Other designs could be implemented.

Referring again specifically to FIG. 6, the tool bit 116 has teeth 150 on its lands 148 that have a constant pitch and constant depth. Such a bit 116, similar to the bit 16 of FIG. 5, can produce constant size particles. The constant pitch and depth may be selected to produce fine, medium or course fragments. The tool bit 216, by contrast, has teeth 250 on its lands 248 that have a variable pitch and a variable depth, and the tool bit 316 has teeth 350 on its lands 348 that have a variable pitch and a constant depth. These tool bits 216 and 316 can produce variable size particles. The tool bits 16, 116, 216, 316, 416 may be formed of stainless steel and/or titanium, by way of example, and may be nickel plated.

Referring again generally to the embodiment of FIGS. 3, 4 and 5, the actuator 20 is rigidly secured to the tool mount 22. In this embodiment, the actuator 20 and tool mount 22 are molded as an integral unit from a medical grade polycarbonate. The tool bit 16 is directly and securely fastened to the tool mount 22, for example, by over molding the tool mount 22 and/or the entire housing 18 onto the bit 16. The actuator 20 includes a power tool interface 24 configured to receive a rotating drive mechanism of a powered tool, not shown, and to impart the rotation of the rotating drive mechanism to the bone milling tool bit 16 through the tool mount 22. In the embodiment of FIG. 4, the power tool interface 24 includes a receptacle 26 for receiving a hexagonal drive bit 28. It will be appreciated that in other embodiments, the receptacle 26 could be configured for other drive bit designs, such as a Phillips bit, a Torx bit, or a slotted bit.

Referring to FIGS. 1, 4 and 5, the actuator 20 in this embodiment includes an outer annular surface 30 with a plurality of indents 32 formed therein to collectively provide a gripping handle. The gripping handle allows a user to manually grind the bone if use of a rotating power tool is not desirable. Thus, the indents 32 on the annular surface 30, combined with the receptacle 26, allow for increased flexibility in the use of the bone mill 10.

Figure 7:
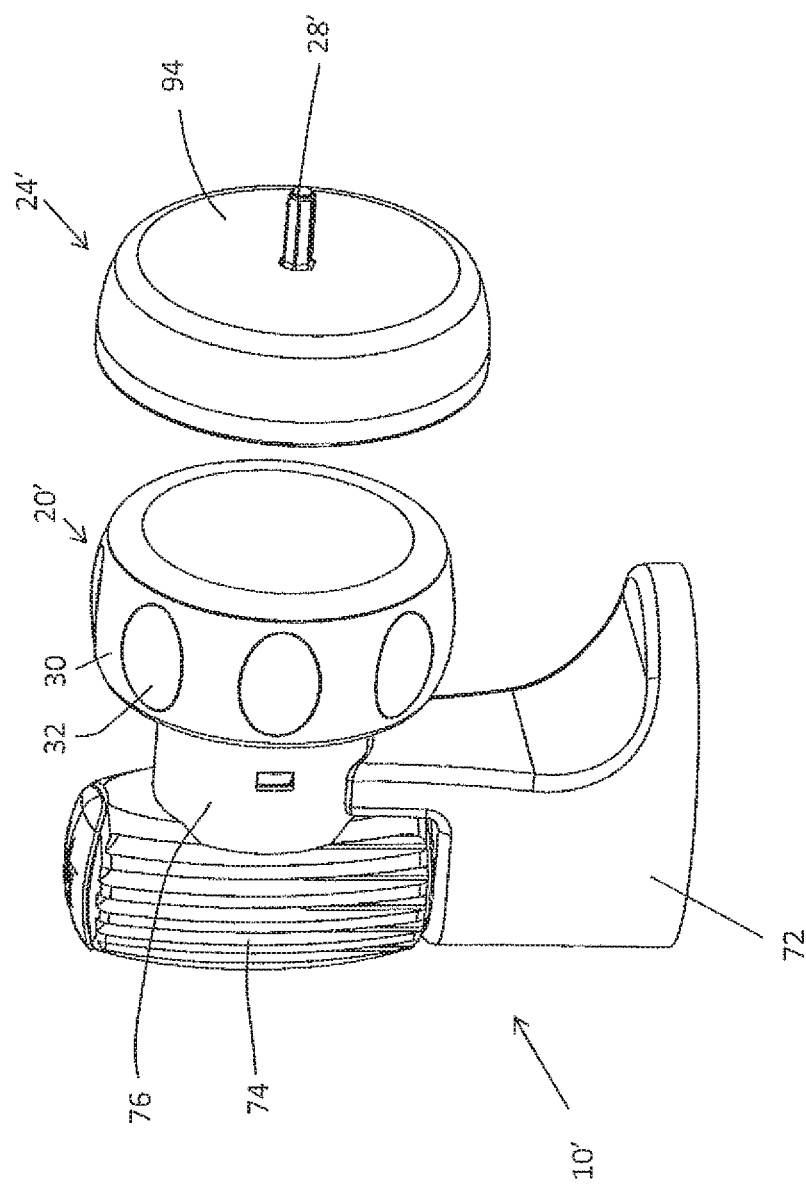
FIG. 7 shows rear perspective view of an alternative embodiment of a bone mill.
Figure 8:
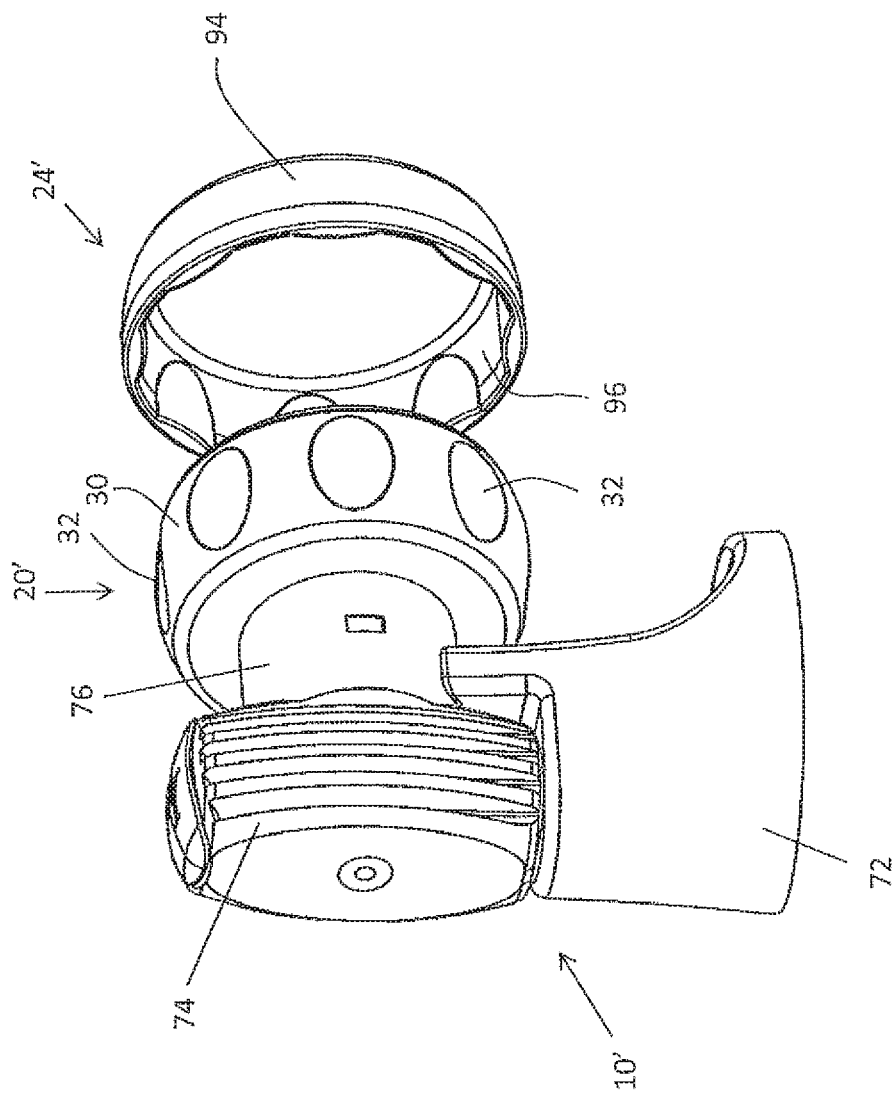
FIG. 8 shows a front perspective view of the bone mill of FIG. 7.

In one alternative shown in FIGS. 7 and 8, the power tool interface 24' is designed as a cap 94 that engages the indents 32 on the annular surface 30, and includes a drive bit 28' rigidly formed therewith. In particular, FIG. 7 shows rear perspective view of an embodiment of the bone mill 10' of FIG. 1 that has substantial similarities to the bone mill 10, except for the power tool interface 24'. FIG. 8 shows a front perspective view of the bone mill 10' of FIG. 7. FIGS. 7 and 8 use the same reference numbers as FIGS. 1-6 for similar elements.

In the embodiment of FIGS. 7 and 8, the cap 94 includes an inner surface 96 that is complementary to, and engages, the annular surface 30 and indents 32. Thus, the power tool, not shown, can be chucked onto the drive bit 28' such that the rotation of the power tool rotates the cap 94 via the drive bit 28'. The engagement between the inner surface 96 of the cap 94 and the indents 32 translates the rotation of the cap 94 to the rotation of the actuator 20', and hence rotation of the bone milling tool bit, not shown in FIGS. 7 and 8. The embodiment of FIGS. 7 and 8 also provide the flexibility of allowing manual rotation of the actuator 20', or mechanized rotation via the cap 94 and its drive bit 28'.

It will be appreciated that the cap 94 may be used with existing bone mills, such as that disclosed in U.S. Pat. No. 7,156,329, which is otherwise designed for manual rotation. The cap 94 may be used to adapt such a tool to be rotated by a mechanized rotating tool.

It will be further appreciated that in still other embodiments, the drive bit (which can be any suitable shaft having a cross-section or gripping flank for connection to a rotating tool) may be integrally formed with the actuator 20.

Figure 9:
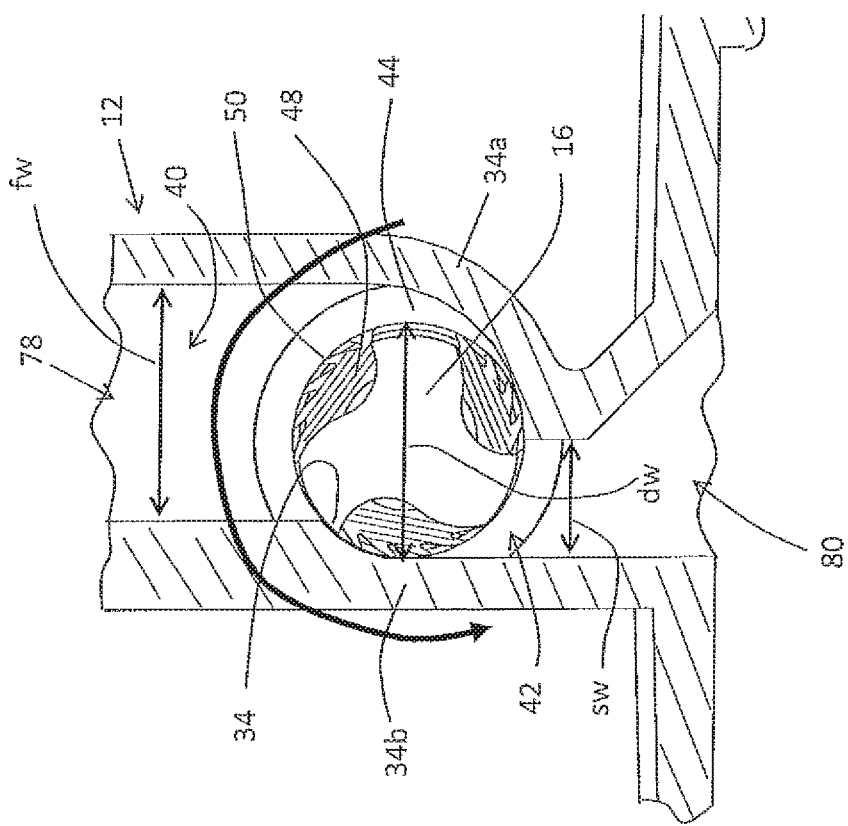
FIG. 9 shows a fragmentary cutaway view of the work chamber and milling tool bit of the bone mill of FIG. 1 taken perpendicular to the axis of rotation.

Referring again generally to FIG. 2, the milling tool bit 16 extends axially through the work chamber 34, and is designed to rotate about the axis to grind bone material in the work chamber 34. FIG. 9 shows a fragmentary cutaway view of the work chamber 34 and milling tool bit 16 taken perpendicular to the axis of rotation R. As shown in FIG. 2, the grinding portion 47 of the milling tool bit 16a extends primarily from the first axial end 36 of the work chamber 34 to the second axial end 38 of the work chamber 34.

The work chamber 34 has a first wall 34a and a second wall 34b that extend axially between the first axial end 36 and the second axial end 38. The work chamber 34 has a largest horizontal width between the first wall 34a and the second wall 34b in which at least a part of the milling tool bit 16 is disposed. The first wall 34a and the second wall 34b define a feed input opening 40 (at the top of the work chamber 34) and an output opening 42 (at the bottom of the work chamber 34). The feed input opening 40 is the open interface between the feed chamber 78 and the work chamber 34, and the output opening 42 is the open interface between the work chamber 34 and the collection chamber 80. The milling tool bit 16 in this embodiment rotates from the first wall 34a to the second wall 34b through the feed input opening 40 and from the second wall 34b to the first wall 34a through the output opening 42.

In accordance with this embodiment, the feed input opening 40 has a first horizontal width fw that is the perpendicular to the axis and is less than the largest horizontal width dw of the work chamber 34 (measured in the same direction). Similarly, the output opening 42 has a second horizontal width sw that is the perpendicular to the axis and is less than the largest horizontal width dw of the work chamber 34 (measured in the same direction). The use of a feed input opening 40 and output opening 42 that are narrower than the widest point of the work chamber 34 creates a crowding action that helps inhibit jamming of the bone into the side. To this end, both the first wall 34a and second wall 34b are arcuately shaped. The first wall 34a preferably is arcuately shaped with an arc radius that is approximately equal to the radius of the OD of the grinding portion 47 of the bone milling tool bit 16, and the arc radius of the second wall 34b exceeds the radius of the OD of the grinding portion 47.

One of the features of the embodiment of FIG. 1 is the inclusion of bearings for rotatably supporting the milling tool bit 16 in at least two points in the housing 12. With reference to FIG. 2, the housing 12 includes a proximal bearing sleeve 44 supported by the housing 12 proximate the first axial end 36 of the work chamber 34, and a distal bearing sleeve 46 supported by the housing 12 proximate the second axial end 38 of the work chamber 34. The bearing sleeves 44, 46 may suitably be formed of metal or a hard polymer, with the remainder of the housing 12 over molded onto them.

Figure 10:
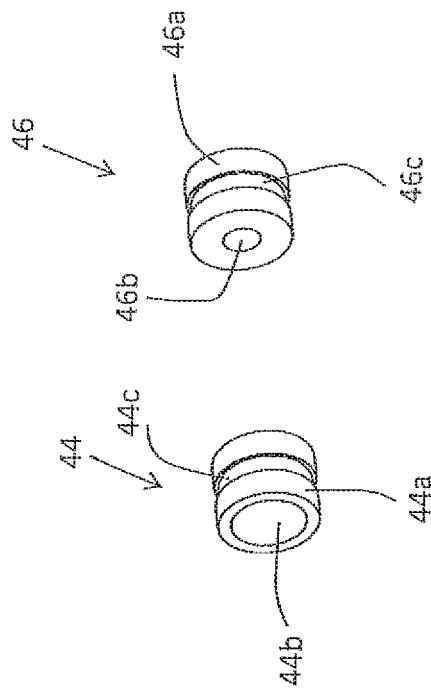
FIG. 10 shows a perspective view of bearing sleeves of the bone mill of FIG. 1 apart from the remainder of the bone mill.

FIG. 10 shows a perspective view of the bearing sleeves 44, 46 apart from the remainder of the bone mill 10. The proximal bearing sleeve 44 is generally in the form of a hollow cylinder having an outer surface 44a, an inner cylindrical surface 44b. The outer surface 44 includes an annular channel 44c that receives a portion of the over molded housing material (see FIG. 2) to fix the axial position of the proximal bearing sleeve 44. It will be appreciated that any other axial discontinuity in the outer surface 44a can serve this purpose. The diameter of the inner cylindrical surface 44a is sufficient to receive, support, and allow rotation of the shank 16a of the milling tool bit 16. Similarly, the distal bearing sleeve 46 is generally in the form of a hollow cylinder having an outer surface 46a, an inner cylindrical surface 46b. The outer surface 46a includes an axial discontinuity in the form of an annular channel 46c that receives a portion of the over molded housing material (see FIG. 2) to fix the axial position of the proximal bearing sleeve 46. The diameter of the inner cylindrical surface 46b is configured to receive, support, and allow rotation of the distal bearing journal 16b of the milling tool bit 16.

With additional reference to FIGS. 2 and 5, the distal bearing journal 16b has a diameter that is smaller than the OD (or largest diameter) of the grinding portion 47 of the milling tool bit 16. Accordingly, the diameter of the inner cylindrical surface 46b is smaller than the OD (largest diameter) of the grinding portion 47. As a consequence, the distal bearing journal 16b also serves to arrest the distal axial movement of the milling tool bit 16. More specifically, in some cases the milling tool 14 is separable from the housing 12 prior to use, and is designed to be manually inserted (axially in the distal or forward direction) into the housing 12 for use. The distal bearing journal 16b can be received by the bearing sleeve 46, but the grinding portion 47 is too wide to fit into the bearing sleeve 46. As a consequence, the distal bearing sleeve 46 in this embodiment sets the axial limit of travel of the milling tool 14 within the housing 12. The tool mount 22 in other embodiments may set the axial travel limit.

Referring again to FIGS. 1 and 2, the bone mill 10 further includes a plunger 60 (FIG. 1) that is configured to fit within, and hence be advanced into, the feed chamber 78 (FIG. 2). In general, the plunger 60 is designed to advance bone fragments (or other materials to be milled) into the work chamber 34 and force the fragments into engagement with the grinding portion 47 of the milling tool bit 16. In this embodiment, the plunger 60 includes at the operative end an actuator button 60a in the form of a curved plate. The plunger 60 also includes at the distal end, within the feed chamber 78, a drive plate, not shown. The drive plate is configured to contact the material to be milled. To this end, the drive plate preferably forms a relatively tight fit with the interior of the feed chamber 78. The plunger 60 further includes shaft or beam 60b that couples actuator butter 60a to the drive plate.

In the general operation of the bone mill 10, the user places material to be milled, for example, bone fragments, into the feed chamber 78, and then inserts the distal end (drive plate) into the feed chamber. The user then inserts the milling tool bit 16 and the tool mount 22 into the cylinder 76 of the housing 12, and advanced the milling tool 14 axially. The milling tool bit 16 advances axially through the inner cylindrical surface 44b of the proximal bearing sleeve (FIG. 10) until the distal bearing journal 16b enters the inner cylindrical surface 46b of the distal bearing sleeve 46b. The engagement of the end of the grinding portion 47 of the milling tool bit 16 with the distal bearing sleeve 46 stops the axial insertion. As a result, the bone mill 10 is complete as shown in FIGS. 1 and 2, with the milling tool 14 assembled with the housing 12.

It will be appreciated that in some embodiments, the milling tool 14 is preassembled into the housing 12. In such an embodiment, the medical professional would not be required to assemble the milling tool 14 and housing 12 as discussed above. In still other embodiments, the housing 12 is packaged as a kit with multiple milling tools. Each milling tool would have the same tool bit housing 18, but having different milling tool bits, such as milling tool bits 16, 116, 216, 316 and/or 416. In this way, the health care facility may stock the same kits for various surgical uses, while giving the user the flexibility to select milling tool bit based on the desired characteristics of the ground bone material.

Once the milling tool 14 and housing 12 are assembled, the user attaches the rotating power tool, not shown, to the milling tool 14 using any of the methods described above in connection with FIG. 4, 7 or 8. For example, in the embodiment of FIG. 4, the user may chuck the drive bit 28 onto the rotating power tool, and then insert the distal end of the drive bit 28 into the receptacle 26. In the example of FIGS. 7 and 8, by contrast, the user may chuck the drive bit 28' of the cap 94 onto the rotating power tool, and place the cap 94 over the outer annular surface 30 of the actuator 20. It will further be appreciated that the rotating power tool may optionally be coupled to the milling tool 14 prior to assembly of the milling tool 14 onto the housing 12.

In any event, once the milling tool 14 is attached to the rotating drive mechanism, the user then applies downward pressure on the plunger 60 while operating the drive mechanism to rotate the actuator 20 (e.g. via drive bit 28). Rotation of the actuator 20 imparts rotational force to the milling tool bit 16 via the tool mount 22. The downward pressure of the plunger 60 forces the bone material from the feed chamber 78 into the work chamber 34 where the rotating grinding portion 47 of the milling tool 16 grinds the material. The ground material exits through the collection chamber 80 and can be later removed for use.

Figure 11:
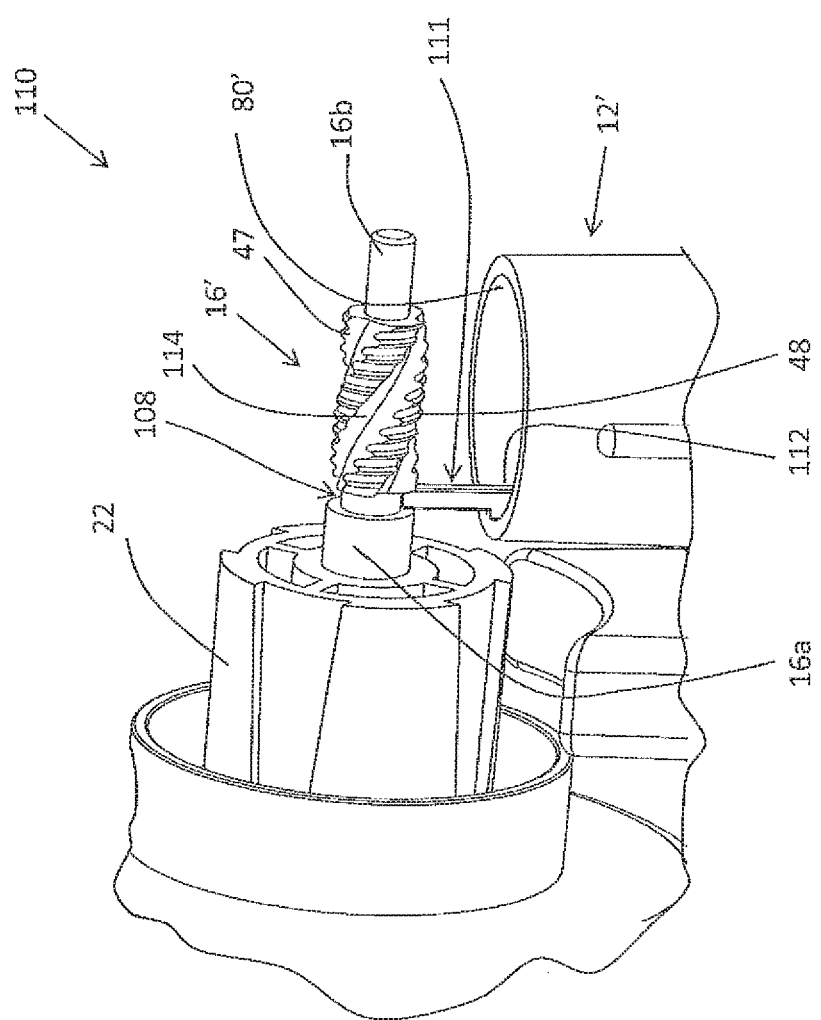
FIG. 11 shows a fragmentary view of a portion of another alternative bone mill that includes a design for scavenging milled bone from the milling tool bit.

FIG. 11 shows a fragmentary view of a portion of an alternative bone mill 110 that has a modification of the bone mill 10 for scavenging milled bone from the milling tool bit. FIG. 11 shows only a portion of the collection chamber 80', the tool mount 22, and a modified milling tool bit 16' apart from the rest of the bone mill 110, which may be otherwise identical to any of the bone mill embodiments described herein. The milling tool bit 16' has a design substantially similar to the milling tool bit 16, except that the milling tool bit has an annular scavenging channel 108 defined between the grinding portion 47 and the shank 16a. The housing 12' has a housing design substantially identical to the housing 12, but further includes a scavenging blade 111 that extends into and substantially fits the scavenging channel. The blade 111 has a shank 112 secured to the housing 12' within the collection chamber 80'.

In the operation of this additional feature, as the milling tool bit 16' rotates due to applied rotational force, milled bone chips travel down machined channels 114 between the lands 48 and are forced into milled bone scavenging channel 108 through Archimedes screw action. As the milled bone collects in the milled bone scavenging channel 108, the scavenging blade 111 scrapes it off to move it to the collection chamber 80'.

Figure 13:
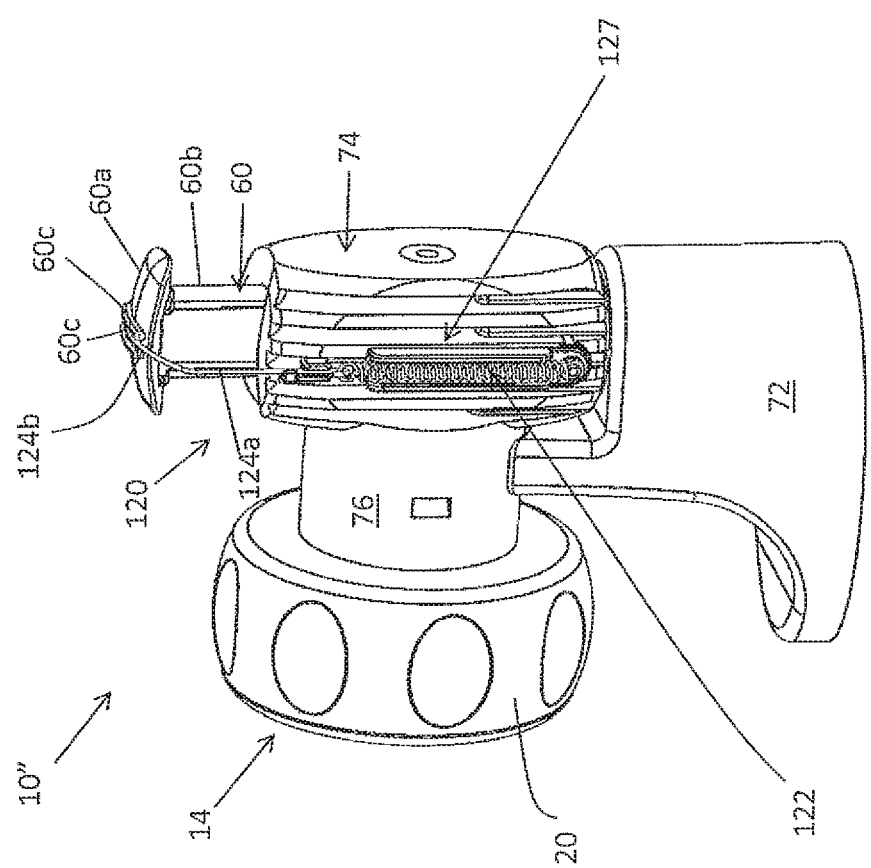
FIG. 13 shows a perspective view of an alternative bone mill 10 that includes the constant pressure mechanism of FIG. 12 in an expanded starting position.
Figure 14:
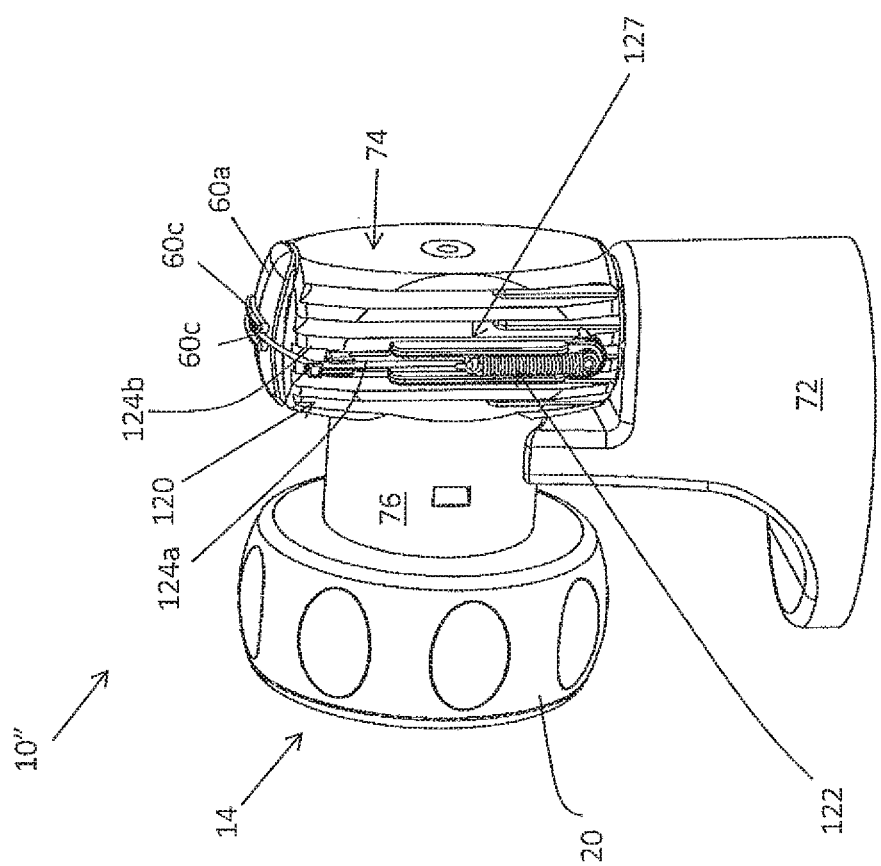
FIG. 14 shows a perspective view of the bone mill of FIG. 13 with the constant pressure mechanism in a contracted end position.

In another alternative embodiment, a bone mill 10" includes a constant pressure mechanism to apply pressure to the plunger 60 without relying on manual user action. In particular, FIG. 12 shows a perspective view of an exemplary constant pressure mechanism 120, FIG. 13 shows a perspective view of a bone mill 10" that includes the constant pressure mechanism 120 in the expanded starting position, and FIG. 14 shows a perspective view of the bone mill 10" with the constant pressure mechanism 120 in the contracted end position.

Figure 12:
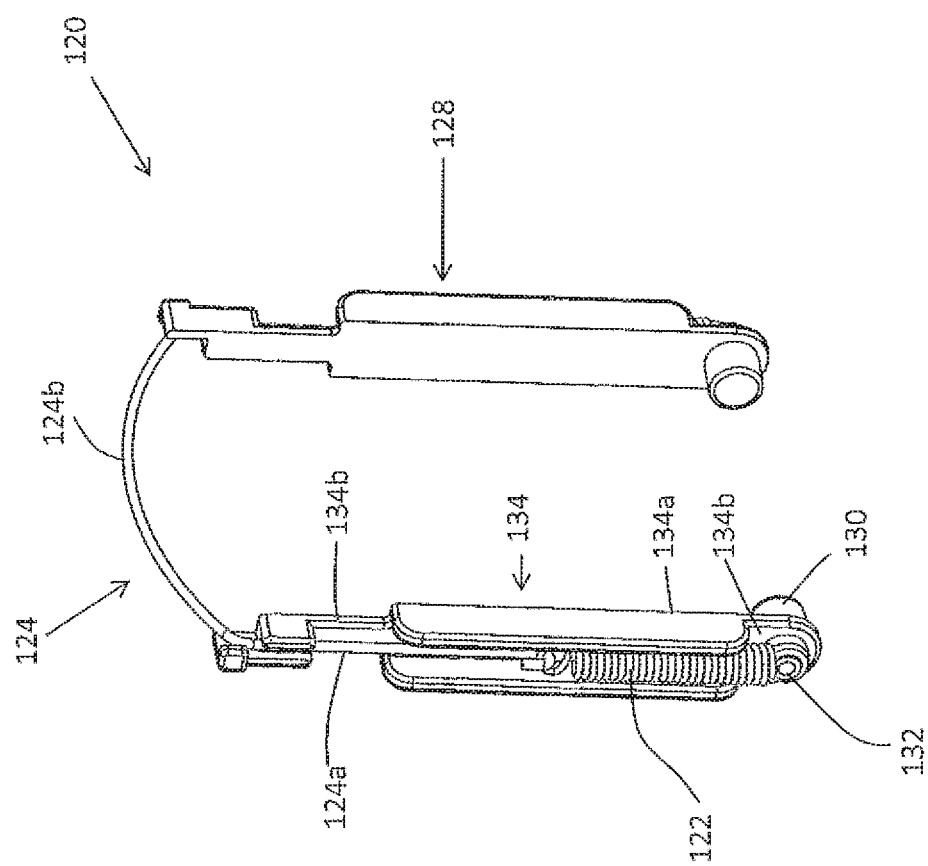
FIG. 12 shows a perspective view of an exemplary constant pressure mechanism.

Referring to FIG. 12, the constant pressure mechanism 120 includes a first spring 122, a metal rod 124, a first guide mount 127, a second guide mount 128, and a second spring, not visible in FIG. 12, but substantially identical in structure and function as the spring 122. The first guide mount 127 includes a knob 130, a post 132, and an elongated track 134.

The track 134 defines a linear guide for the spring 122 and a portion of the metal rod 124. The cylindrical knob 130 extends from a first side 134a of the track 134 and is configured to be received by a correspondingly shaped opening in the housing 12. The post 132 extends from the second side 134b of the track on which the spring 122 rides. The second guide mount 128 has a substantially identical construction.

The metal rod 124 includes a first vertical portion 124a, an arcuate middle portion 124b, and a second vertical portion, not shown, but which is substantially identical to the first vertical portion 124a. The first and second guide mounts 127, 128 are spaced apart by a distance approximately equal to the width of the barrel 74 of the housing 12 (see FIGS. 13 and 14), and are suitably aligned parallel to each other in this embodiment. With additional reference to FIGS. 13 and 14, the middle portion 124b of the metal rod 124 extends above the barrel 74 between the first vertical portion 124a and second vertical portion. In general, the metal rod 124 may be mostly rigid, but flexible rod such as the material of a wire hanger.

The first vertical portion 124a includes a hooked end to connect to a first end of the spring 122. The second end of the spring is secured to the post 132. The spring 122 is a spring chosen to provide a relatively constant force between the expanded position as shown in FIG. 13 and the contracted position in FIG. 14. Without external force, the spring 122 biases towards the contracted position shown in FIG. 14. The second vertical portion and second spring are configured in an analogous way with respect to the second guide mount 128.

In the above-described configuration, the first spring 122 and the second spring are operable coupled (via the metal rod 124 and the guide mounts 127, 128) to provide a bias force against the plunger 60 to move the plunger 60 within the feed chamber 78 toward the work chamber 34 (see FIG. 2). In particular, FIGS. 13 and 14 show the mechanism 120 mounted onto the housing 12. To this end, the knob 130 is received into an opening, not shown, the side of the barrel 74, and the knob of the second guide mount 128, not shown in received into an opening in the opposite side of the barrel 74. The metal rod 124 is spring biased to hold the knob 130 and the opposing knob in place.

The middle portion 124b of the metal rod bears against the actuator button 60a of the plunger 60. To this end, the plunger 60 may include linear ridges 60c forming a channel that receives and holds the middle portion 124b in place.

In operation, the user pulls the middle portion 124b of the metal rod 124 off of the button actuator 60a and rotates it to the side, to allow the plunger 60 to be removed. The cylindrical design of the knob 130 allows for rotation of the mechanism 120 without removing the mechanism from the housing 12. The user may then place bone material into the feed chamber 78, and replace the plunger 60 into the feed chamber 78. The user may then rotate the metal rod 124 and place the middle portion 124b in the channel between the linear ridges 60c on the plunger 60. The resulting starting position is shown in FIG. 13.

The user may then release the metal rod 124. The bias of the spring 122 (and opposing spring) causes the spring 122 and opposing spring to contract, urging the metal rod 124 downward against toward the finishing contracted position shown in FIG. 14. The middle portion 124b of the metal rod 124 bears against the plunger 60 to move the plunger 60 downward in the feed chamber 78. The downward movement of the plunger 60 forces the bone material into the work chamber 34. In this embodiment, the user need not manipulate both the power rotation tool and the plunger 60. Indeed, the constant force mechanism 120 can provide such an advantage even if the mechanism 120 does not provide force that is constant. The movement of the plunger 60 would nevertheless be hands-free. It will also be appreciated that other configurations of rods and/or devices may be used to translate the force of the spring 122 (and/or another spring) to the downward motion of the plunger 60. Moreover, it will be appreciated that the advantages of using at least one spring to apply force to the plunger 60 has advantages even in bone mills having manual only rotation means.

Figure 15:
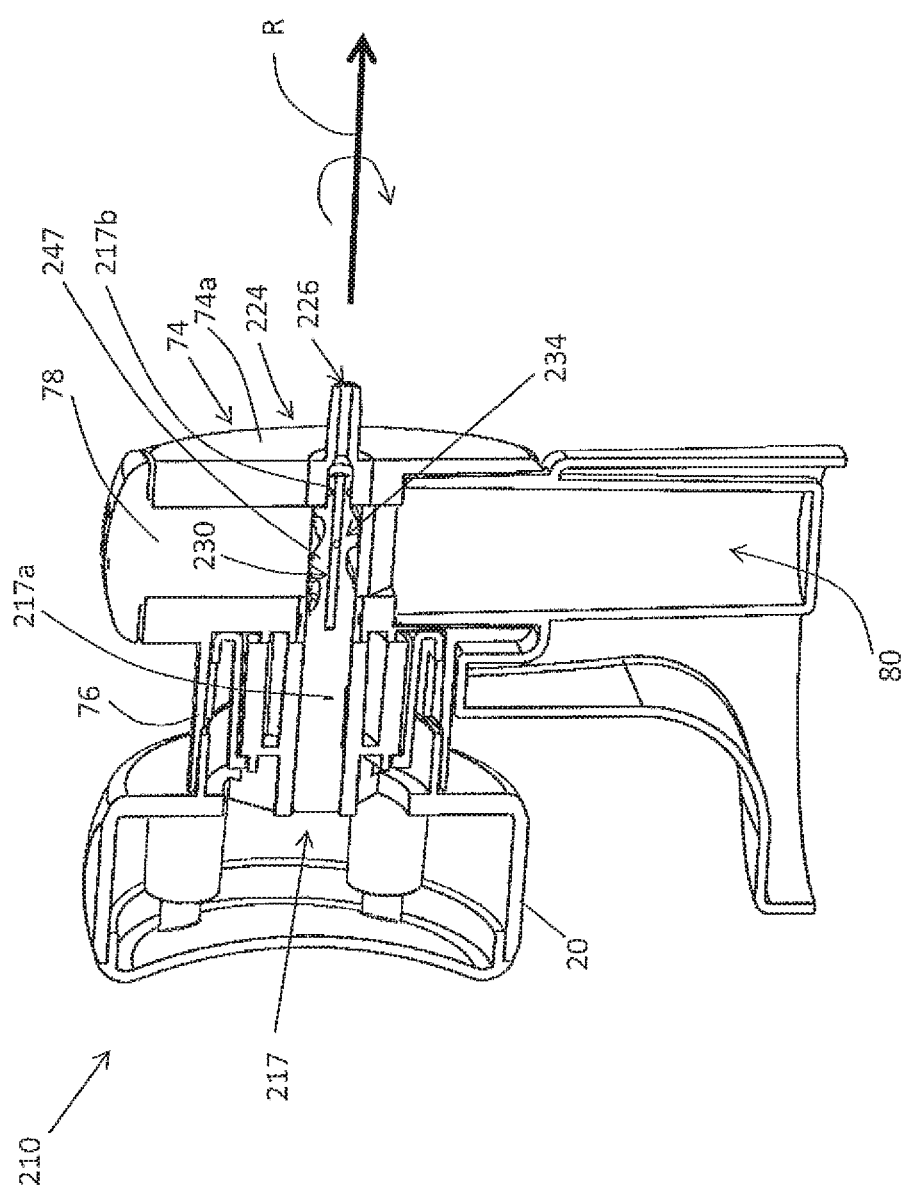
FIG. 15 shows a cutaway perspective view of an alternative bone mill that includes a mechanism for adding fluid to a material being milled.
Figure 16:
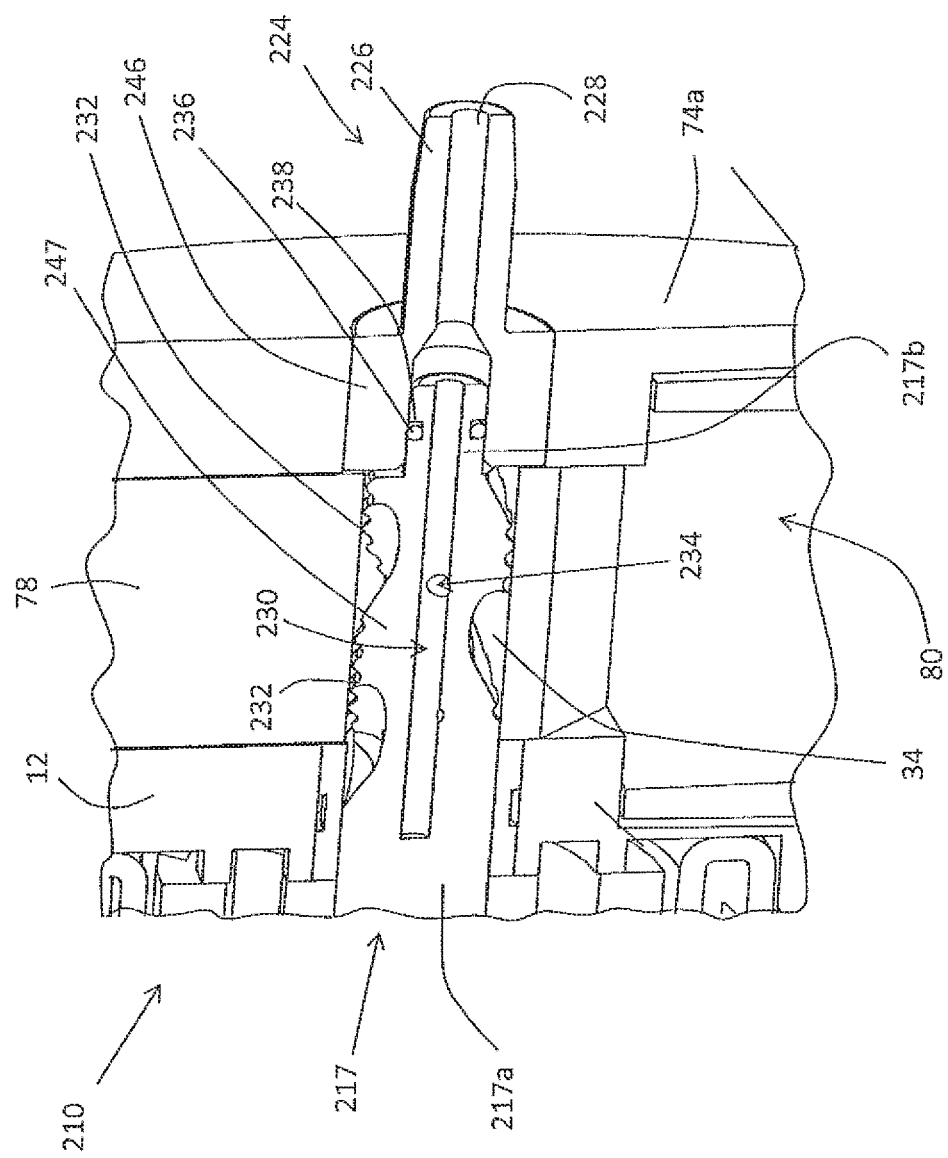
FIG. 16 shows an enlarged, fragmentary cutaway view of the bone mill of FIG. 15b.

Another feature of one or more embodiments relates to the delivery of fluid that may be used to mix with the ground bone to form bone cement useful in surgery. FIG. 15 shows a cutaway perspective view of an alternative bone mill 210 that includes a mechanism for adding fluid to a material being milled. The bone mill 210 is otherwise substantially identical to the bone mill of FIG. 1, and like reference numbers are used to identify like structures in the embodiments of FIGS. 1 and 15. FIG. 16 shows an enlarged, fragmentary cutaway view of the bone mill 210.

With reference to FIGS. 15 and 16, the bone mill 210 includes a housing 212 that is substantially identical to the house 12 of FIG. 1, except that the housing 212 further includes an axial port 224. The axial port 224 is a nozzle 226 that extends from front wall 74a of the barrel 74. As shown more clearly in FIG. 16, the nozzle 226 includes an interior channel 228 and extends into the front wall 74a of the barrel 74. In this embodiment, the nozzle 226 may be integral with a larger cylindrical structure that forms the distal bearing sleeve 246. As shown in FIGS. 15 and 16, the nozzle 226 is disposed such that the interior channel 228 is aligned with the axis of rotation R.

This embodiment also includes a bone milling tool bit 217 that has a bore 230 that defines a central axial channel. The milling tool bit 217 includes a shank 217a, a distal bearing journal 217b, and a grinding portion 247 therebetween. The grinding portion 247 includes lands and teeth 232 that may take any suitable form such as those shown in FIGS. 5 and 6. The bore 230 extends from the distal end of the distal bearing journal 217b at least partially and preferably fully through the grinding portion 247. The grinding portion 247 also includes one or more distribution channels 234 that extend outward from the bore 230 to and through the outer surface of the grinding portion 247. The bore 230 and distribution channels 234 thus form a fluid connection between the axial end of the tool bit 217 and the work chamber 34 of the housing. The distal bearing journal 246 also includes a ring seal 236 disposed in an annular channel 238.

In general, the bone 210 may be operated in the same manner as the bone mill 10 of FIG. 1. However, fluid is also hydrodynamically forced into axially mounted port 224, and specifically, into the interior channel 228. The fluid may be any desired fluid for mixing bone cement, for example, bone marrow aspirate or orthobiologics. The fluid flows under pressure from the interior channel 228 of the nozzle 226 to the bore 230 of the milling tool bit 217. The fluid advances through the bore 230 and out of the distribution channels 234 to the work chamber 34. The fluid therein mixes with the material being milled, e.g. bone, to at least begin the process of mixing the bone cement.

It will be appreciated that in embodiments in which the bone mill 210 is intended for more than a single use, the axial port 224 and milling tool bit 217 may be used instead for flushing the bone mill 210 with sterilizing fluids.

Figure 17:
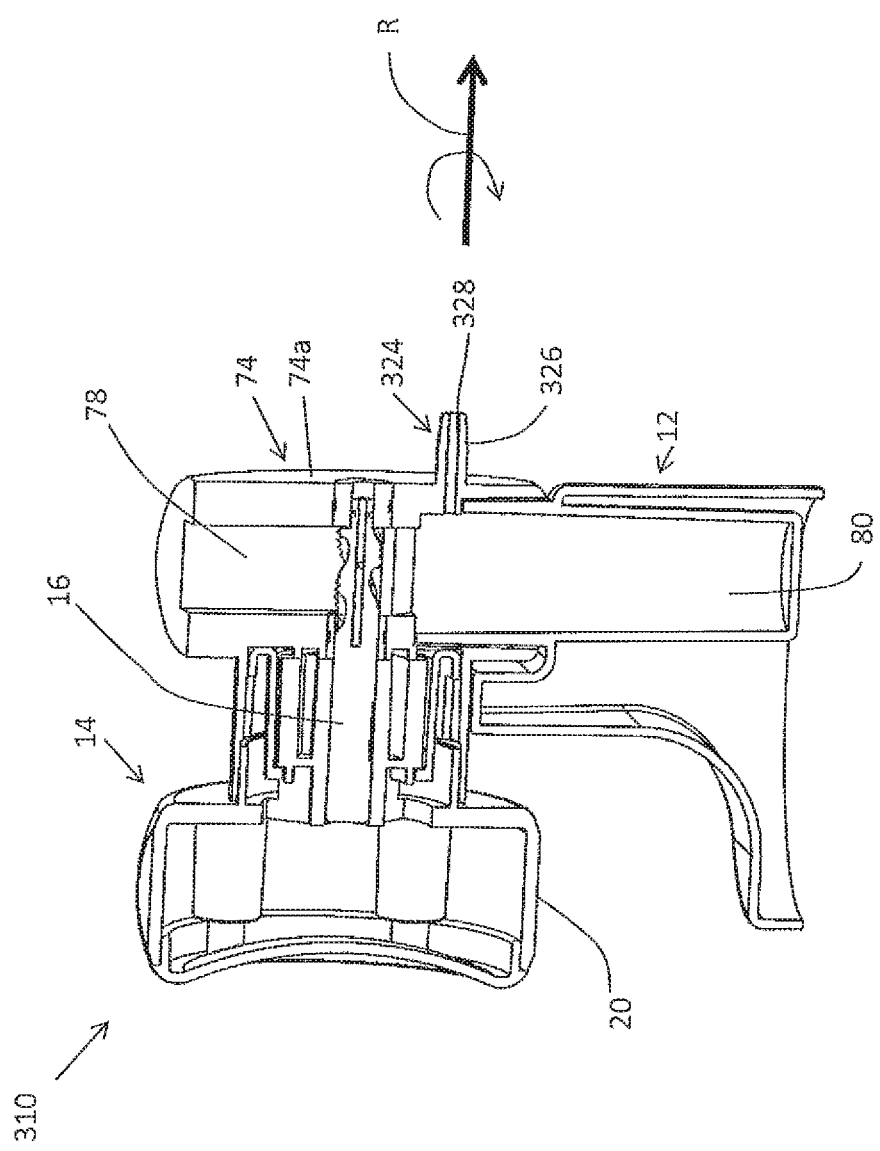
FIG. 17 shows a cutaway perspective view of an alternative bone mill that includes a different mechanism for adding fluid to a material being milled.

In other alternatives of bone mills that include a fluid port, the introduction of fluid may occur in other portions of the bone mill. To this end, FIG. 17 shows a cutaway view of a bone mill 310 that is identical to the bone 10 of FIG. 1, except that the bone mill 310 includes a fluid port 324 that is disposed on the front face 74a of the barrel 74 at a vertical level below the axis R. The fluid port 324 includes a nozzle 326 that may suitably have a similar structure as the nozzle 226 of FIG. 16, including an interior fluid channel 328. The interior channel 328 extends into and feeds directly into the collection chamber 80.

Figure 18:
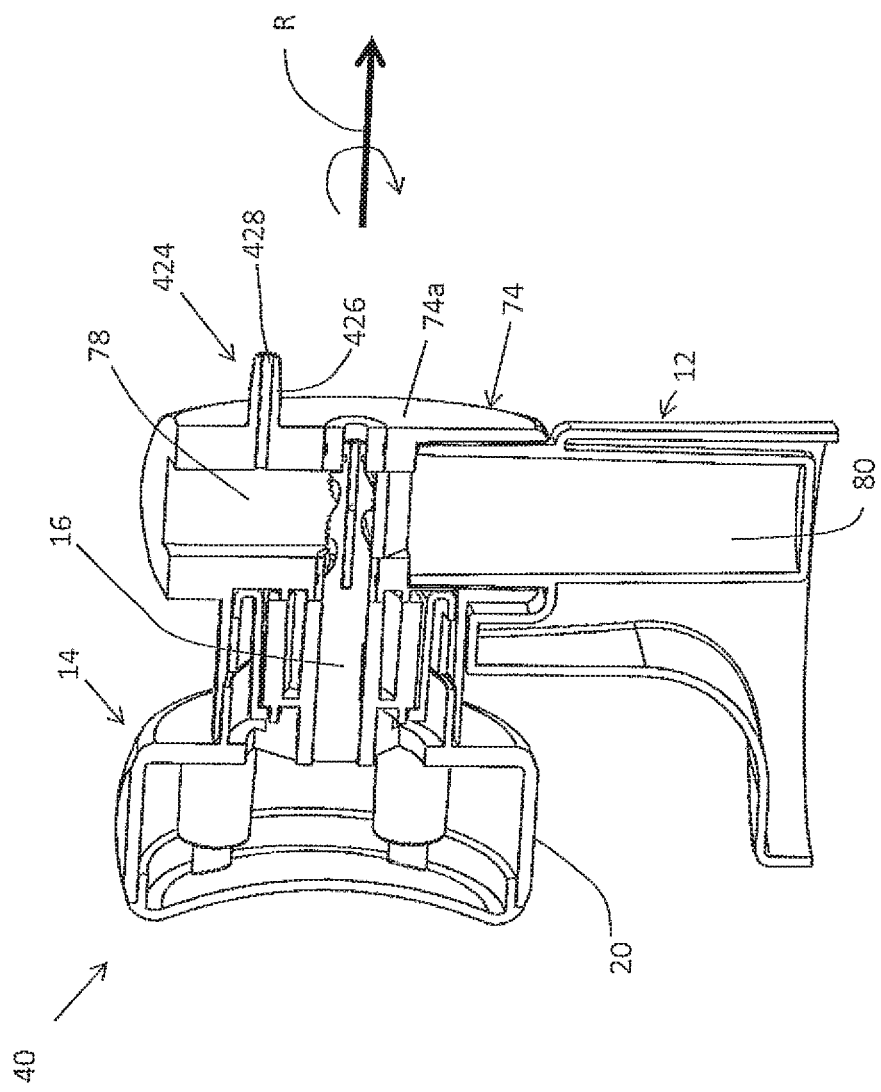
FIG. 18 shows a cutaway perspective view of an alternative bone mill that includes yet another mechanism for adding fluid to a material being milled.

FIG. 18 shows a cutaway view of another embodiment of a bone mill 410 that is identical to the bone 10 of FIG. 1, except that the bone mill 410 includes a fluid port 424 that is disposed on the front face 74a of the barrel 74 at a vertical level above below the axis R. The fluid port 424 includes a nozzle 426 that may suitably have a similar structure as the nozzle 226 of FIG. 16, including an interior channel 428. The interior channel 428 extends into and feeds the feed chamber 78.

It will be appreciated that the above described embodiments are merely illustrative, and that those of ordinary skill in the art may readily devise their own modifications and implementations that incorporate the principles of the present invention and fall within the spirit and scope thereof. For example, the various inventive features described herein may be implemented together or separately, and can be implemented on other bone mill designs. For example, the various features described herein may be implemented on bone mills having different milling tool bit designs, including designs having multiple milling tool bits. Likewise, other inventive features can be adapted to existing variants.

What is claimed is:

1. A bone mill, comprising:
   a housing defining a work chamber, the work chamber having a first axial end, a second axial end, a first wall extending between the first axial end and the second axial end, and a second wall extending between the first axial end and the second axial end;
   at least a first bone milling tool configured to be disposed within the work chamber, and extending at least from the first axial end to the second axial end,
   a proximal bearing sleeve supported by the housing proximate the first axial end, and a distal bearing sleeve supported by the housing proximate the second axial end, said proximal bearing sleeve and said distal bearing sleeve configured to support said first milling tool and allow rotation of the first milling tool within the work chamber about an axis; and
   wherein
   the first wall and the second wall define a feed input opening and an output opening;
   the first bone milling tool has a grinding portion configured to be disposed in the work chamber, the work chamber having a largest horizontal width from the first wall to the second wall in a first direction perpendicular to the axis; and
   the feed input opening has a first horizontal width from the first wall to the second wall in the first direction that is less than the largest horizontal width.

2. The bone mill of claim 1, wherein the output opening of the work chamber has a second horizontal width perpendicular to the axis that is less than the largest horizontal width.

3. The bone mill of claim 1, wherein at least one of the first wall and the second wall of the work chamber has an arcuate surface having an arcuate axis parallel to the axis.

4. The bone mill of claim 1, wherein the housing further comprises a feed chamber in fluid communication with the work chamber via the feed input opening, and wherein the bone mill further comprises a plunger configured to be received in the feed chamber to advance bone material within the feed chamber into the work chamber.

5. The bone mill of claim 4, further comprising a least one spring supported by the housing and operably coupled to provide a bias force against the plunger to move the plunger within the feed chamber toward the work chamber.

6. The bone mill of claim 5 wherein the at least one spring comprises a first spring and a second spring, wherein the bone mill further comprises a metal rod extending from the first spring to the second spring such that a portion of the metal rod bears against the plunger, and wherein the metal rod is operably coupled between the first spring and the second spring such that bias force of the spring causes the portion of the metal rod to urge the plunger within the feed chamber toward the work chamber.

7. The bone mill of claim 6, wherein the first bone milling tool comprises a milling tool bit that includes the grinding portion, further includes a shank and a distal bearing journal, the shank disposed at least in part in the proximal bearing sleeve, and the distal bearing journal disposed at least in part in the distal bearing sleeve, wherein the distal bearing journal has a diameter that is smaller than a diameter of the grinding portion.

8. The bone mill of claim 1, wherein the first bone milling tool comprises a milling tool bit that includes the grinding portion, further includes a shank and a distal bearing journal, the shank disposed at least in part in the proximal bearing sleeve, and the distal bearing journal disposed at least in part in the distal bearing sleeve, wherein the distal bearing journal has a diameter that is smaller than a diameter of the grinding portion.

9. The bone mill of claim 1, wherein the first bone milling tool comprises a milling tool bit that includes a grinding portion, a shank and a distal bearing journal, the shank disposed at least in part in the proximal bearing sleeve, and the distal bearing journal disposed at least in part in the distal bearing sleeve.

10. The bone mill of claim 9, wherein the distal bearing journal has a diameter that is smaller than a diameter of the grinding portion.

11. The bone mill of claim 1, wherein at least a portion of the first wall in the work chamber is concave, and at least a portion of the second wall in the work chamber is concave.

12. A bone mill, comprising:
   a housing defining a work chamber, the work chamber having a first axial end, a second axial end, a first wall extending between the first axial end and the second axial end, and a second wall extending between the first axial end and the second axial end;
   at least a first bone milling tool configured to be disposed within the work chamber, and extending at least from the first axial end to the second axial end,
   a proximal bearing sleeve supported by the housing proximate the first axial end, and a distal bearing sleeve supported by the housing proximate the second axial end, said proximal bearing sleeve and said distal bearing sleeve configured to support said first milling tool and allow rotation of the first milling tool within the work chamber about an axis,
   wherein the first bone milling tool comprises a milling tool bit that includes a grinding portion, a shank, and an annular channel disposed between the grinding portion and the shank; and wherein the housing includes a blade configured to extend into the channel, the blade configured to scrape material within with the channel.

* * * * *